(12) United States Patent
Gottardo et al.

(10) Patent No.: US 8,975,408 B2
(45) Date of Patent: Mar. 10, 2015

(54) MOXIFLOXACIN HYDROCHLORIDE COMPOUNDS AND INTERMEDIATES AND METHODS FOR MAKING SAME

(71) Applicant: F.I.S. -Fabbrica Italiana Sintetici S.p.A., Alte di Montecchio Maggiore (Vincenz (IT)

(72) Inventors: Gianni Gottardo, Vigonovo (IT); Pierluigi Padovan, Casale sul Sile (IT); Sergio Osti, Padua (IT)

(73) Assignee: F.I.S.—Fabbrica Italiana Sintetici S.p.A., Montecchio Maggiore (VI) (IT)

( * ) Notice: Subject to any disclaimer, the term of this patent is extended or adjusted under 35 U.S.C. 154(b) by 0 days.

(21) Appl. No.: 14/158,939

(22) Filed: Jan. 20, 2014

(65) Prior Publication Data

US 2014/0135501 A1 May 15, 2014

Related U.S. Application Data

(62) Division of application No. 13/543,896, filed on Jul. 9, 2012, now Pat. No. 8,664,398.

(30) Foreign Application Priority Data

Jul. 29, 2011 (IT) .............................. TO2011A0705

(51) Int. Cl.
| | | |
|---|---|---|
| *C07D 215/38* | (2006.01) | |
| *A61K 31/04* | (2006.01) | |
| *C07D 471/04* | (2006.01) | |
| *C07D 401/04* | (2006.01) | |

(52) U.S. Cl.
CPC ............ *C07D 471/04* (2013.01); *C07D 401/04* (2013.01)
USPC .......................................... 546/159; 514/312

(58) Field of Classification Search
USPC .......................................... 514/312; 546/159
See application file for complete search history.

(56) References Cited

U.S. PATENT DOCUMENTS

| 6,270,799 B1 * | 8/2001 | Siefert et al. ................... 424/474 |
| 6,383,471 B1 * | 5/2002 | Chen et al. ....................... 424/45 |
| 7,759,362 B2 * | 7/2010 | Guo et al. ...................... 514/312 |

FOREIGN PATENT DOCUMENTS

| CN | 101817820 A | 9/2010 |
| EP | 1992626 A1 | 11/2008 |

OTHER PUBLICATIONS

Fischer & C. Robin Ganellin J. Ed, The Chemical Evolution of Moxifloxacin (Extract), Analogue-Based Drug Discovery, Feb. 13, 2007, p. 337, Weinheim: Wiley-Vch.

M. Lalitha Devi, K.B. Chandrasekhar, A Validated, Specific Stability-Indicating RP-LC Method for Moxifloxacin and Its Related Substances, Chromatographia, An International Journal for Rapid Communication in Chromatography, Electrophoresis and Associated Techniques, Mar. 21, 2009, pp. 993-999, vol. 69 No. 9/10, Vieweg + Teubner | GWV Fachverlage GmbH.

Y. Ravindra Kumar, V.V.N.K.V. Prasad Raju, R. Rajesh Kumar, S. Eswaraiah, K. Mukkanti, M.V. Suryanarayana, M. Satyanarayana Reddy, Structural identification and characterization of impurities in moxifloxacin, Journal of Pharmaceutical and biomedical analysis, Nov. 26, 2003, pp. 1125-1129, vol. 34, Elsevier B.V., New York, USA.

* cited by examiner

*Primary Examiner* — D M Seaman
(74) *Attorney, Agent, or Firm* — Robert E. Alderson, Jr.

(57) ABSTRACT

Methods for producing moxifloxacin hydrochloride compounds having very low levels of impurities are provided. Compounds produced using such methods and pharmaceutical compositions including such compounds are also provided.

2 Claims, 7 Drawing Sheets

MOXIFLOXACIN HYDROCHLORIDE COMPOUNDS AND INTERMEDIATES AND METHODS FOR MAKING SAME

CROSS REFERENCE TO RELATED APPLICATION

This application is a divisional of U.S. application Ser. No. 13/543,896 filed Jul. 9, 2012 which claims benefit of Italian Patent Application No. TO2011A000705 filed Jul. 29, 2011, the contents of which are incorporated by reference in their entirety. To the extent appropriate, a claim of priority is made to each of the above disclosed applications.

FIELD OF THE INVENTION

The present invention relates to the pharmaceutically active ingredient known as moxifloxacin hydrochloride and intermediates thereof.

BACKGROUND OF THE INVENTION

Moxifloxacin is a broad-spectrum fluoroquinolonic antibacterial agent, used for the treatment of respiratory infections (pneumonia, chronic sinusitis, chronic bronchitis) sold in form of hydrochloride by Bayer AG under the name of Avelox® and Avalox®. It is also sold by Alcon Inc. in a low dosage form for ophthalmic use under the name of Vigamox®.

Moxifloxacin, of formula (II) and having the chemical name of 3-quinolinecarboxylic, 1-cyclopropyl-6-fluoro-1,4-dihydro-8-methoxy-7-[(4aS,7aS)-octahydro-6H-pyrrole[3,4-b]pyridine-6-yl]-4-oxo-acid, is characterized by a fluoroquinolonic skeleton, which is common to that of two other antibiotics of the same category (Gatifloxacin and Balofloxacin) and by a side chain constituted by (4aS,7aS)-octahydro-1H-pyrrole[3,4-b]pyridine.

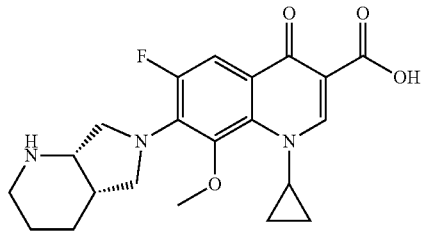

(II)

The fluoroquinolonic intermediate of formula (V), with the 8-methoxy group is a commercial product.

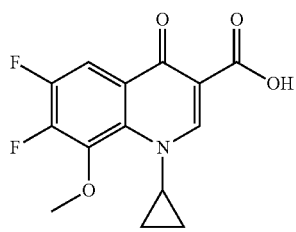

(V)

(4aS,7aS)-Octahydro-1H-pyrrole[3,4-b]pyridine, also referred to as (S,S)-2.8-Diazabycyclo[4.3.0]nonane and having CAS RN [151213-40-0] and formula (VI),

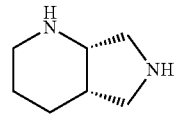

(VI)

constitutes the side chain of moxifloxacin, is the key intermediate of the synthesis in that it has two chiral centers, both having an S configuration, and is optically active and levogyre. The preparation of this key intermediate is also described in patent applications MI2009A001353 and WO2010/100215 both owned by F.I.S. Fabbrica Italiana Sintetici S.p.A. These references provide, respectively, for a process for optimising the optical resolution and a regio and stereoselective synthesis process of the bioenzymatic type.

A first synthesis process of moxifloxacin hydrochloride described in EP 550903 includes the coupling reaction between the 1-Cyclopropyl-6,7-difluoro-1,4-dihydro-8-methoxy-4-oxo-3-quinolinic acid of formula (V):

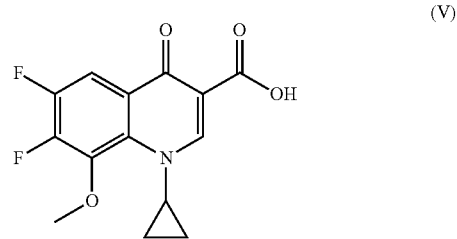 [SMILES: COc1c(F)c(F)cc2c(=O)c(C(=O)O)cn(C3CC3)c12]

(V)

with the (4aS,7aS)-Octahydro-1H-pyrrole[3,4-b]pyridine intermediate of formula (VI) in the presence of a base:

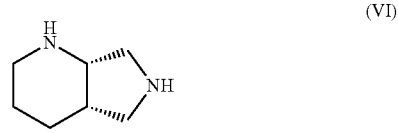

(VI)

Due to the low regioselectivity of the reaction, the product obtained contains the 6-isomer impurity of formula (VIII):

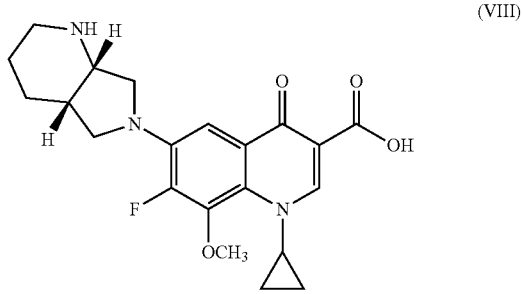 [SMILES: COc1c(F)c(N2C[C@@H]3CCCN[C@@H]3C2)cc2c(=O)c(C(=O)O)cn(C3CC3)c12]

(VIII)

as greater impurity, which—being a position isomer—is difficult to separate from the product, without significantly reducing its yield.

Chromatographic purification on a silica gel column leads to similarly low yields.

WO 2008/138759 describes a process for the preparation of moxifloxacin hydrochloride monohydrate where the coupling reaction between 1-cyclopropyl-6,7-difluoro-1,4-dihydro-8-methoxy-4-oxo-3-quinolinic acid of formula (V) with (S,S)-2.8-diazabycyclo[4.3.0]nonane of formula (VI) is carried out in the absence of a base and moxifloxacin is isolated as L-tartrate or fumarate or p-ditoluoyltartrate with the aim of purifying it from the greater impurity, i.e. the 6-isomer of formula (VIII). It is then converted into moxifloxacin hydrochloride.

Another synthesis process of moxifloxacin is described in WO 2005/012285 includes the reaction between the ethyl ester of 1-cyclopropyl-6,7-difluoro-1,4-dihydro-8-methoxy-4-oxo-3-quinolinic acid of formula (IX):

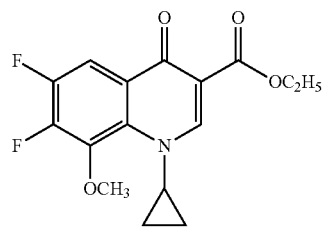

(IX)

with boric acid and acetic anhydride to form an intermediate borate complex with 95% yield which is then reacted with (4aS,7as)-Octahydro-1H-pyrrole[3,4-b]pyridine of formula (VI) with 72% yield. After this the ester and the complex are hydrolysed, and salification is carried out to give moxifloxacin hydrochloride with a 91% yield, for an overall 62% molar yield.

In WO 2008/059223 a process similar to the previous one is employed except that the complex is generated using boric acid and propionic anhydride instead of acetic anhydride.

A fourth process, described in WO 2006/134491, provides for the reaction of 1-cyclopropyl-6,7-difluoro-1,4-dihydro-8-methoxy-4-oxo-3-quinolinic acid of formula (V) with boron trifluoride etherate to provide a difluoroborate intermediate which is reacted with (S,S)-2.8-diazabycyclo[4.3.0]nonane of formula (VI) in presence of a base with a 92% yield providing a difluoroborate complex of moxifloxacin which is then hydrolized and salified to provide moxifloxacin hydrochloride with an overall yield ranging from 42 to 55%.

In addition, the synthesis of moxifloxacin has been conducted, as described in EP 1832587, through a process similar to the previous one, carried out via a one-pot method and including silanization before complexation through boron trifluoride.

The processes described above lead to unsatisfactory yields and require the use of toxic reagents such as boron trifluoride.

An alternative process which overcomes these problems and especially that of the 6-isomer impurity is described in the U.S. patent application Ser. No. 13/051,081 and Italian patent application MI2010A000450 both owned by F.I.S. Fabbrica Italiana Sintetici S.p.A. where magnesium salt is used for performing the coupling between the 1-Cyclopropyl-6,7-difluoro-1,4-dihydro-8-methoxy-4-oxo-3-quinolinic acid of formula (V) with the intermediate (4aS,7as)-Octahydro-1H-pyrrole[3,4-b]pyridine of formula (VI) thus avoiding the formation of the 6-isomer impurity of formula (VIII).

The above-described prior art processes for the preparation of moxifloxacin in their entirety require the use of coupling between the two syntons described previously. Such coupling also requires the inherent formation of another typical well known impurity of moxifloxacin referred to as 3-quinolinecarboxylic, 1-cyclopropyl-6-fluoro-1,4-dihydro-8-methoxy-7-[(4aS,7aS)-1-methyloctahydro-6H-pyrrole[3,4-b]pyridine-6-yl]-4-oxo-acid, having the formula (VII):

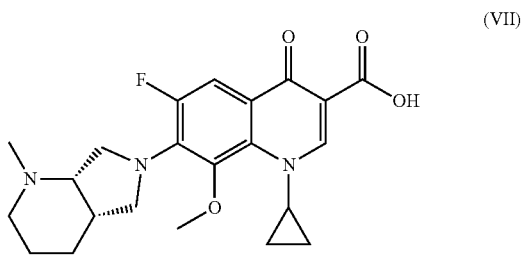 [SMILES: COc1c(N2C[C@@H]3CCCN(C)[C@@H]3C2)c(F)cc2c(=O)c(C(=O)O)cn(C3CC3)c12]

(VII)

This impurity having the number CAS 721970-37-2 was identified and published for the first time by Dr. Reddy's Laboratories Ltd., Bulk Actives Unit-III, Hyderabad, AP (India) in the Journal of Pharmaceutical and Biomedical Analysis (2004), 34(5), 1125-1129 where it is called Impurity-1. It was observed to be present in amounts above 0.1% in industrially produced moxifloxacin.

In the publication of the United States Pharmacopeia-India Private Limited (USP-India) on Chromatographia (2009), 69 (9-10), this impurity referred to as Imp-1 was correctly defined as a process impurity. The samples used by USP-India to carry out the study were provided by Dr. Reddy's Laboratories Ltd. The developed HPLC method allows detecting such impurity in moxifloxacin with a 0.016% detectability limit.

This reference as well as our own experimentation confirm that the impurity of formula (VII) is a typical process impurity of moxifloxacin. Its formation appears to be due to the action of hydrofluoric acid, released during the coupling of the two syntons on the methoxy group in position 8 which releases the methyl carbocation which in turn alkylates a second moxifloxacin molecule. This impurity is particularly difficult to remove from the product using conventional re-crystallization methods.

SUMMARY OF THE INVENTION

The present invention provides methods for the preparation of moxifloxacin hydrochloride having unexpected and surprisingly low levels of the impurity 3-quinolinecarboxylic, 1-cyclopropyl-6-fluoro-1,4-dihydro-8-methoxy-7-[(4aS,7aS)-1-methyloctahydro-6H-pyrrole[3,4-b]pyridine-6-yl]-4-oxo-acid (formula (VII)).

Further characteristics and advantages of the methods and compositions according to the present invention will be apparent from the description outlined below.

DETAILED DESCRIPTION

The present invention provides novel methods for the preparation of moxifloxacin hydrochloride of formula (I):

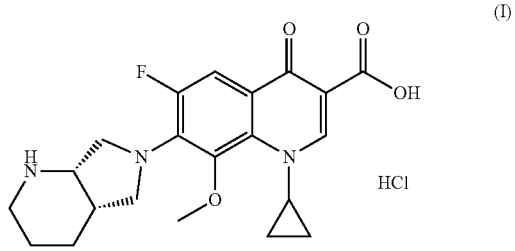 [SMILES: COc1c(N2C[C@@H]3CCCN[C@@H]3C2)c(F)cc2c(=O)c(C(=O)O)cn(C3CC3)c12 ; Cl]

(I)

comprising the following steps:
(a) salification of base moxifloxacin of formula (II):

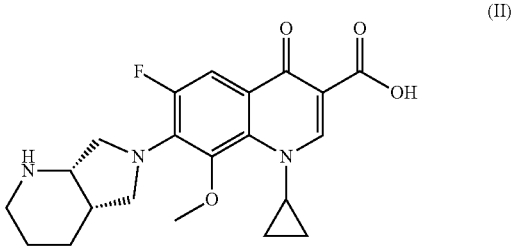 [SMILES: COc1c(N2C[C@@H]3CCCN[C@@H]3C2)c(F)cc2c(=O)c(C(=O)O)cn(C3CC3)c12]

(II)

with a sulfonic acid of formula (III):

(III)

wherein R is a C1-C12 linear or branched alkyl or an aryl, to provide a compound of formula (IV):

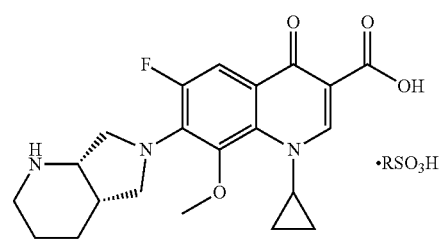

(IV)

(b) optional purification of the compound of formula (IV), and
(c) conversion of the compound of formula (IV) into moxifloxacin hydrochloride of formula (I).

It was discovered that preparing the salts of moxifloxacin with sulfonic acids alone results in moxifloxacin and salts thereof having surprisingly and unexpectedly low levels of the impurity of formula (VII).

As described herein the other methods of preparation of moxifloxacin salts do not allow purifying the product from the impurity of formula (VII) equivalent to the compound salts of formula (IV) of the present invention, i.e. using the moxifloxacin salts with sulfonic acids. The preparation of some moxifloxacin salts different from the sulfonic acids revealed that the amount of such impurity is even increased thus confirming the insolubility of such impurity with respect to moxifloxacin itself.

The quantification in percentage area of the formula (VII) impurity content in moxifloxacin and salts thereof may be carried out through the HPLC method indicated in Example 5.

The residue R of the sulfonic acid used according to the process of the invention is a C1-C12 linear or branched alkyl or an aryl. In particular R alkyl may be a methyl, ethyl, propyl, butyl, pentyl, hexyl, heptyl, octyl, nonyl, decyl, undecyl, docecyl and it may be linear or branched. R may thus also be isopropyl, n-propyl, n-butyl, isobutyl, sec-butyl, n-pentyl, isopentyl, etc. In particular R aryl may be phenyl, tolyl(p-methylphenyl), xylyl, benzyl, naphthyl, indolyl, nosyl, etc.

In certain embodiments, R is selected from among C1-C4 alkyl, phenyl and tolyl. In other embodiments R is methyl or ethyl or tolyl. Thus, moxifloxacin mesylate or moxifloxacin tosylate are compounds encompassed by the present invention.

Figure 1:
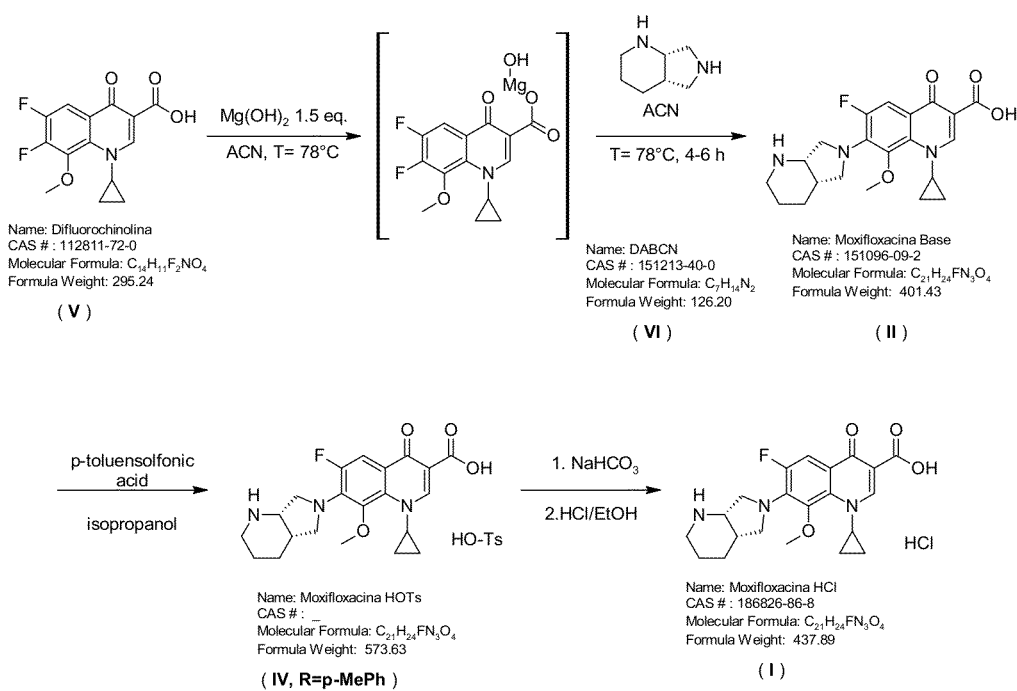
FIG. 1 illustrates a representative synthesis scheme of moxifloxacin hydrochloride according to the present invention.

In certain embodiments the synthesis of moxifloxacin hydrochloride may be performed as shown in FIG. 1.

With the aim of carrying out screening of solvents in which various moxifloxacin salts are to be prepared, with the final aim of evaluating the capacity thereof to purify moxifloxacin, the acids indicated in the first column of the table below were used.

Preparations were carried out in different alcoholic solvents, as indicated in the first line of table I.

TABLE I

| ACID | Methanol | Ethanol | Isopropanol | Benzylalcohol |
|---|---|---|---|---|
| Acetic acid | — | — | — | — |
| Formic Acid | — | — | — | — |
| Hydrochloric acid | X | X | X | — |
| Phosphoric Acid | X | X | X | — |
| Oxalic Acid | — | — | X | — |
| Succinic Acid | — | — | — | — |
| Bromidric Acid | X | X | X | X |
| Anhydrous Citric Acid | X | — | — | — |
| Tartaric Acid | — | — | — | — |
| P-toluenesulfonic Acid | X | X | X | — |
| Methanesulfonic Acid | — | X | X | — |

The "–" symbol means that there was no precipitation of moxifloxacin salt from the tested solvent, while "X" means that the relative salt was isolated. The experiment was conducted using 5 solvent volumes, 1.05 molar equivalents of acid and carrying out the isolation of the salt by filtration at ambient temperature.

Methods according to the present invention provide for the reduction of the amount of impurity of formula (VII) in moxifloxacin hydrochloride from up to 5% to values below 0.15%, for example, in a range of about 0.05% to about 0.15%. In particular, for formula (VII) impurity content at levels between about 1.2% and about 5% it is recommended to carry out optional step (b) with one or more purifications of the compound of formula (IV) while for contents lower than 1.2% optional step (b) is usually not necessary. The initial moxifloxacin, obtained through the procedure described in Example 1, normally has a formula (VII) impurity content ranging from about 0.8% to about 1.2% and thus typically step (b) does not need to be carried out.

Methods of the present invention can thus provide moxifloxacin hydrochloride having between about 0.05% and about 0.15% of impurity of formula (VII) and in some embodiments between about 0.06% and about 0.14%, and in some embodiments between about 0.06% and about 0.09%, and in other embodiments about 0.08% of such impurity.

Step (a) may be carried out starting from a moxifloxacin base isolated or present in solution, for example in a solution coming from the synthesis thereof by coupling two syntons of formula (V) and (VI). Step (a) may be carried out in an organic solvent, such as a C1-C4 alcohol such as methanol, ethanol, n-propanol, isopropanol, n-butanol, isobutanol, sec-butanol, tert-butanol. In certain embodiments it is carried out in isopropanol. Sulfonic acid may be added in solid form or in a solution of an organic solvent, preferably in the same solvent in which the moxifloxacin base is solubilised.

dichloromethane and isopropanol mixture, while the aqueous phase may contain sodium bicarbonate. Subsequently the moxifloxacin base phase may be converted into moxifloxacin hydrochloride through treatment using concentrated hydrochloric acid in ethanol.

A further unexpected advantage of methods according to the present invention is that preparing the salts of formula (IV), besides reducing the formula (VII) impurity content, also allows increasing both the chemical purity and the optical purity of moxifloxacin.

Comparative Table II below summarises the capacity of various moxifloxacin salts to remove or increase the formula (VII) impurity content in moxifloxacin and increase the chemical purity thereof. In the first line data are indicated regarding the initial moxifloxacin that was used.

TABLE II

| Acid used in step (a) | Moxifloxacin salt obtained | Impurity (VII) HPLC A % | Moxi Purity HPLC A % | A %(VII) salt/ A %(VII) Moxi. |
|---|---|---|---|---|
| — | Initial Moxifloxacin | 1.77% | 72.77% | — |
| Hydrochloric acid | Hydrochloride | 1.54% | 93.45% | 87% |
| Phosphoric Acid | Phosphate | 2.31% | 76.34% | 131% |
| Bromidric Acid | Bromohydrate | 2.22% | 86.75% | 125% |
| Oxalic Acid | Oxalate | 1.88% | 87.38% | 106% |
| — | Initial Moxifloxacin | 1.84% | 85.64% | — |
| Naphthalene disulfonic acid | Naphthalenedisulphate (1:1) | 1.85% | 95.06% | 100% |
| Naphthalene disulfonic acid | Naphthalenedisulphate (2:1) | 1.32% | 96.12% | 71% |
| Methanesulfonic acid | Methanesulfonate | 0.78% | 87.26% | 42% |
| Ethanesulfonic Acid | Ethanesulfonate | 0.70% | 98.52% | 38% |
| — | Initial Moxifloxacin | 1.09% | 90.27% | — |
| P-toluenesulfonic acid | Tosylate | 0.54% | 98.64% | 50% |
| — | Initial Moxifloxacin | 1.38% | 89.55% | — |
| P-toluenesulfonic acid | Tosylate | 0.73% | 98.45% | 53% |
| — | Initial Moxifloxacin | 1.79% | 91.01% | — |
| p-toluenesulfonic acid | Tosylate | 0.82% | 98.55% | 46% |

Step (b) is optional and provides for the purification of the compound of formula (IV) through one or more re-crystallizations or pulping thereof in an organic solvent, with the possible addition of water. Step (b) may be carried out in an isopropanol and water mixture. In certain embodiments it is constituted by one or two pulpings. This optional step allows for the reduction in the amount of impurity of formula (VII) and can be conveniently used when the initial moxifloxacin has a formula (VII) impurity content greater than about 1.2% (HPLC A %).

According to the present invention step (c) may provide for the direct conversion of the moxifloxacin salts of formula (IV) in moxifloxacin hydrochloride or such conversion may be carried out with the following two steps:

(c1) conversion of the compound of formula (IV) in moxifloxacin base of formula (II), (c2) salification of moxifloxacin base of formula (II) with hydrochloric acid resulting in moxifloxacin hydrochloride of formula (I).

Methods for the direct conversion of moxifloxacin salts of formula (IV) in moxifloxacin hydrochloride may be carried out in presence of concentrated hydrochloric acid, ethanol and water. The conversion with two steps may be carried out by firstly releasing moxifloxacin from the salt thereof by extracting in an organic solvent in the presence of a base in the aqueous phase. The organic phase may be constituted by a The initial moxifloxacin having been prepared according to methods described in U.S. patent application Ser. No. 13/051,081 owned by F.I.S. Fabbrica Italiana Sintetici S.p.A., is free of isomer-6 impurity of formula (VIII) and thus it was not possible to evaluate the advantages deriving from methods according to the present invention with respect to such other typical process impurities.

The preparations of moxifloxacin salts indicated in Table II were carried out obtaining the moxifloxacin base in isopropanol and adding the corresponding acid in suitable amounts.

Figure 3:
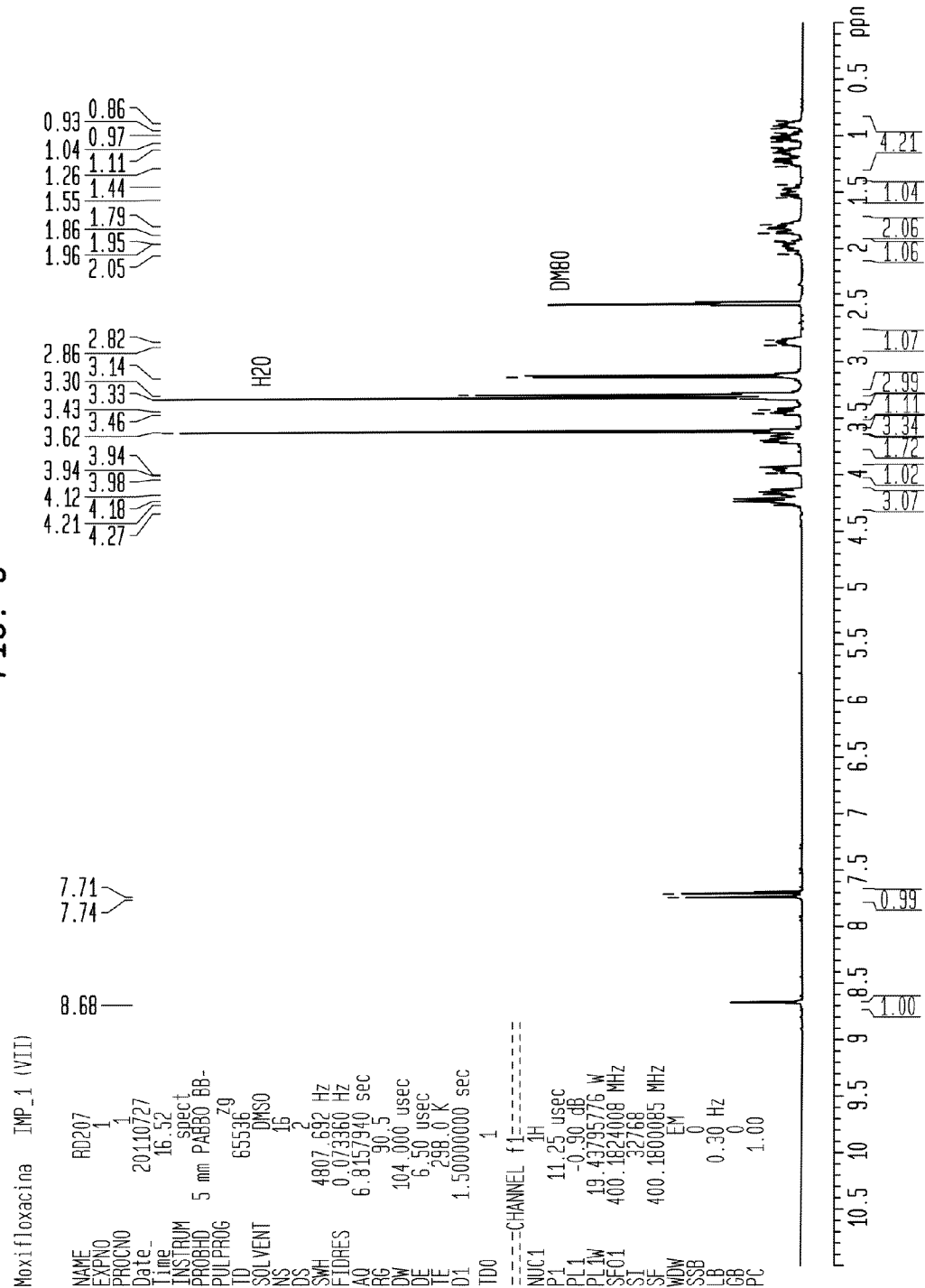
FIG. 3 illustrates a 1H-NMR spectrum of the impurity of moxifloxacin of formula VII).

Table II shows that the salts of formula (IV) according to the embodiments of the present invention, i.e. the moxifloxacin salts with sulfonic acids, resulting in moxifloxacin having a low formula (VII) impurity content, typically between about 0.5% and about 0.9%, well below the levels obtained, for example, with the moxifloxacin salt with oxalic acid, or with hydrobromic acid where the impurity even increases (see the last column with a ratio between the amount of the impurity (VII) in the prepared salt and initial one in the initial moxifloxacin). The preparation of the tosylate salt allows for the reduction of the amount of such impurity by about 50%. In certain embodiments impurity (VII) provides characteristic 1H-NMR spectra as shown in FIG. 3. The present invention also provides for moxifloxacin salts of stoichiometry 1 mole of naphtalenedisulfonic acid for two moles of moxifloxacin called moxifloxacin naphtalendisulphonate (2:1). In certain embodiments the two sulfonic groups are in position 1 and 5 on the naphthalene ring.

Figure 2:
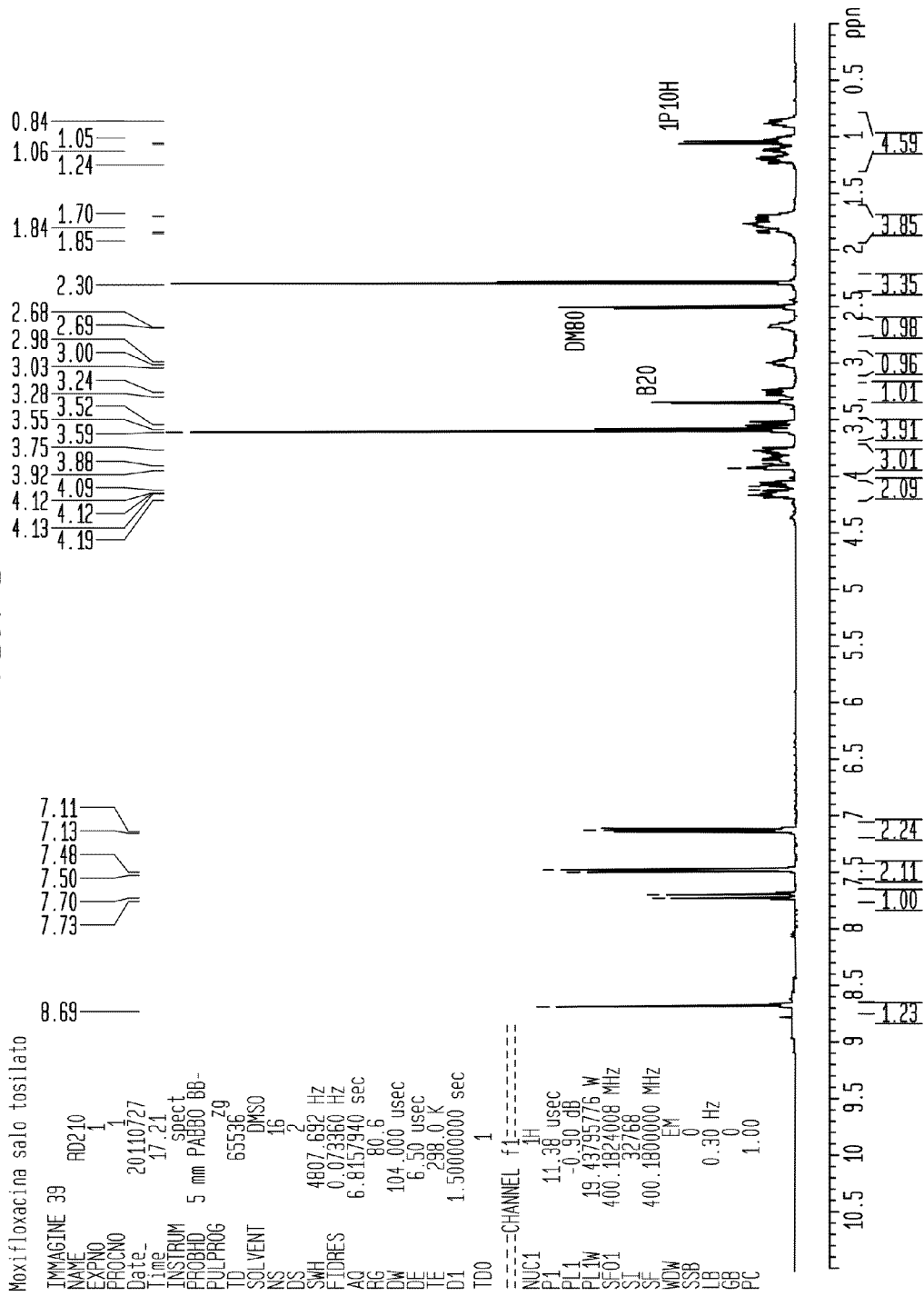
FIG. 2 illustrates a 1H-NMR spectrum of moxifloxacin tosylate according the present invention.
Figure 4:
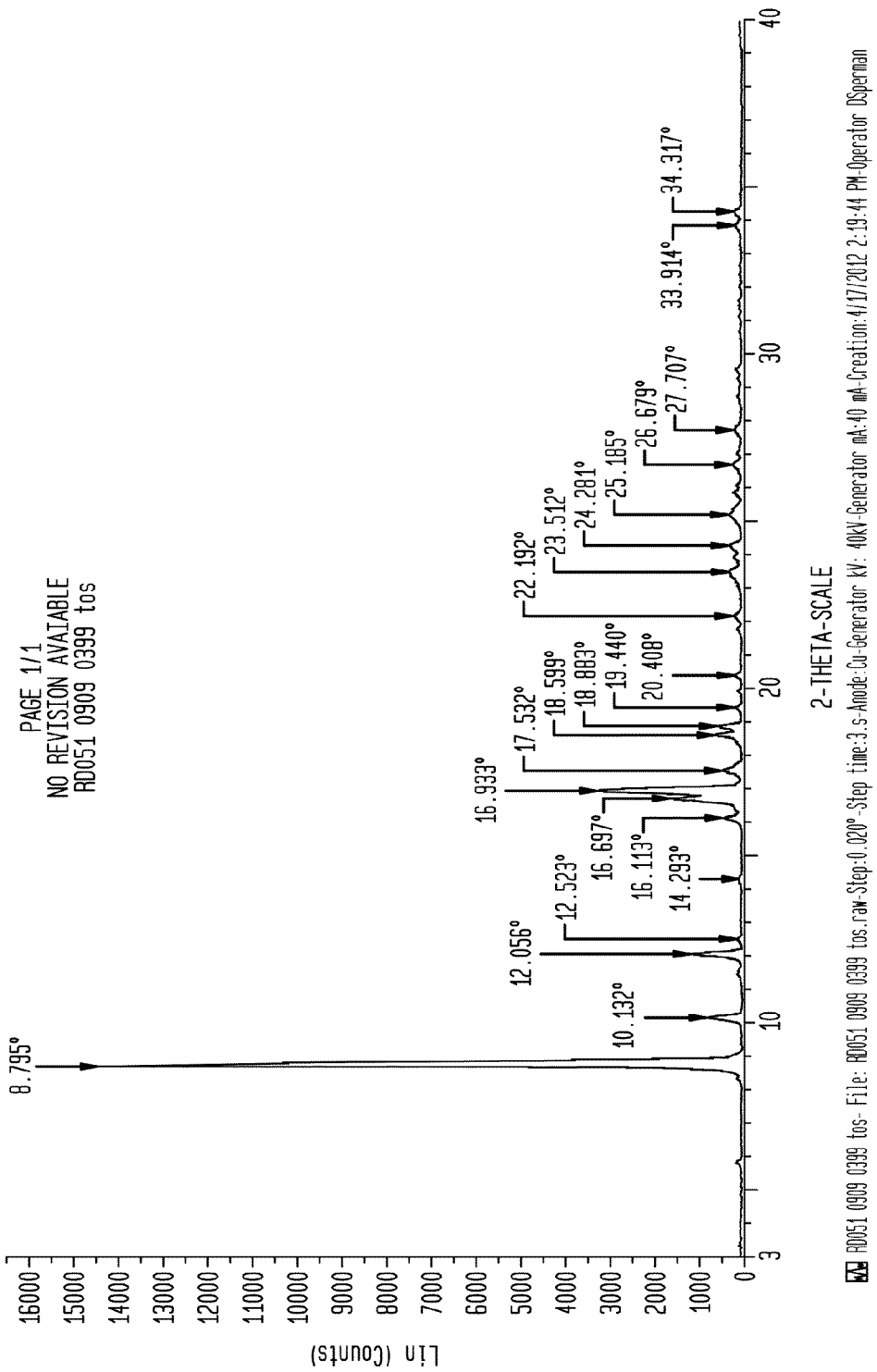
FIG. 4 shows the X-Ray Powder Diffraction (XPRD) difractogram of moxifloxacin tosylate including parameters of the analysis.

The preparation of moxifloxacin tosylate according to the present invention is especially useful. Moxifloxacin tosylate prepared according to embodiments of the invention provides characteristic 1H-NMR spectra as shown in FIG. 2. Moxifloxacin tosylate prepared according to such methods also provides a crystalline solid which exhibits a characteristic X-Ray Powder Diffraction (XRPD) pattern with characteristic peaks expressed in 2-Theta value: 8.8, 10.2, 12.1, 16.7, 17.0 (+/−) 0.1 (see FIG. 4). We refer to this crystalline form as Form I.

Figure 5:
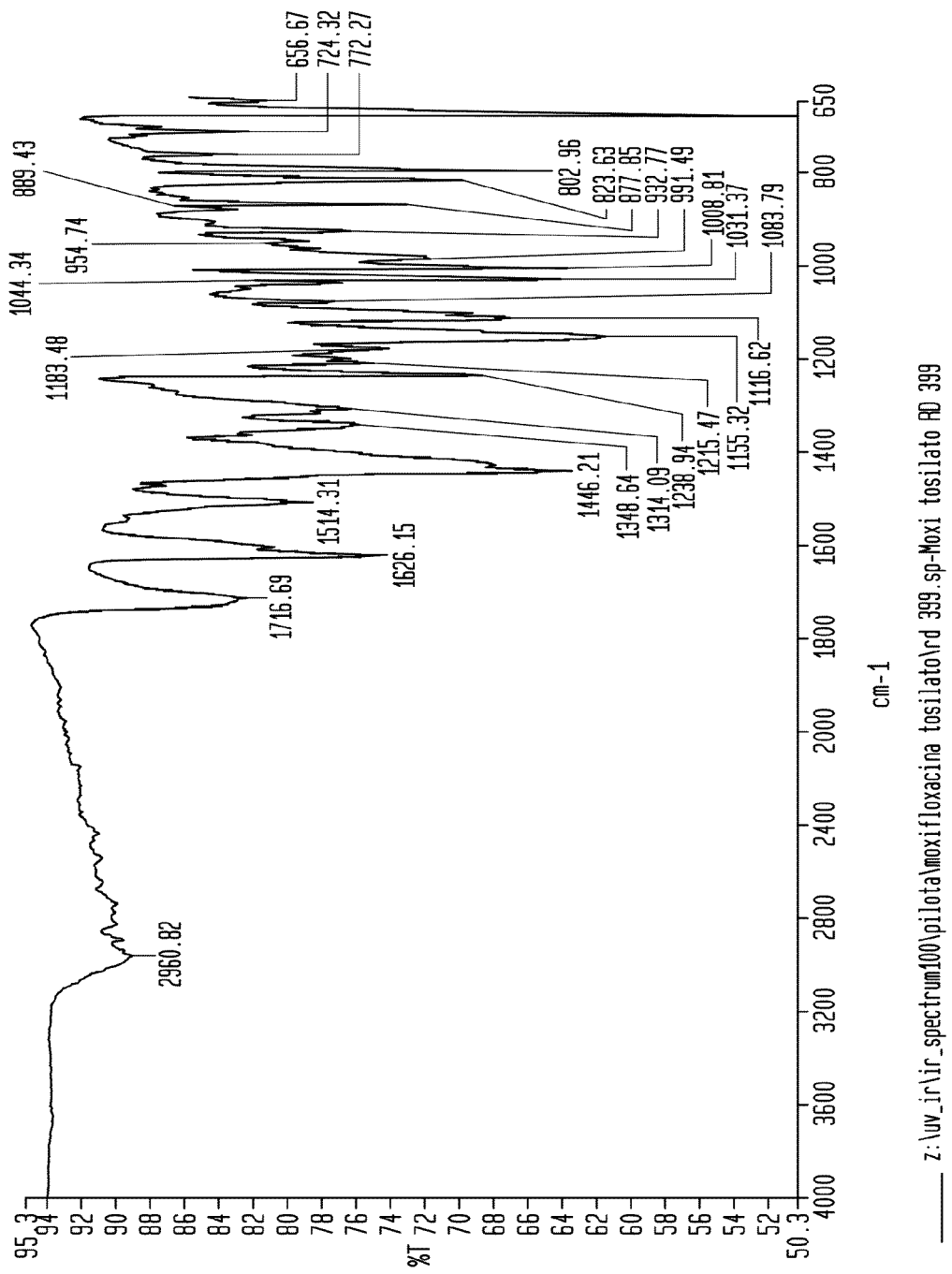
FIG. 5 shows the FT-IR spectrum of moxifloxacin tosylate.

In addition, moxifloxacin tosylate shows an FT-IR spectrum having the following peaks: 1717, 1626, 1446, 1239, 1155, 1031, 1009, 803 cm-1 (see FIG. 5).

Figure 6:
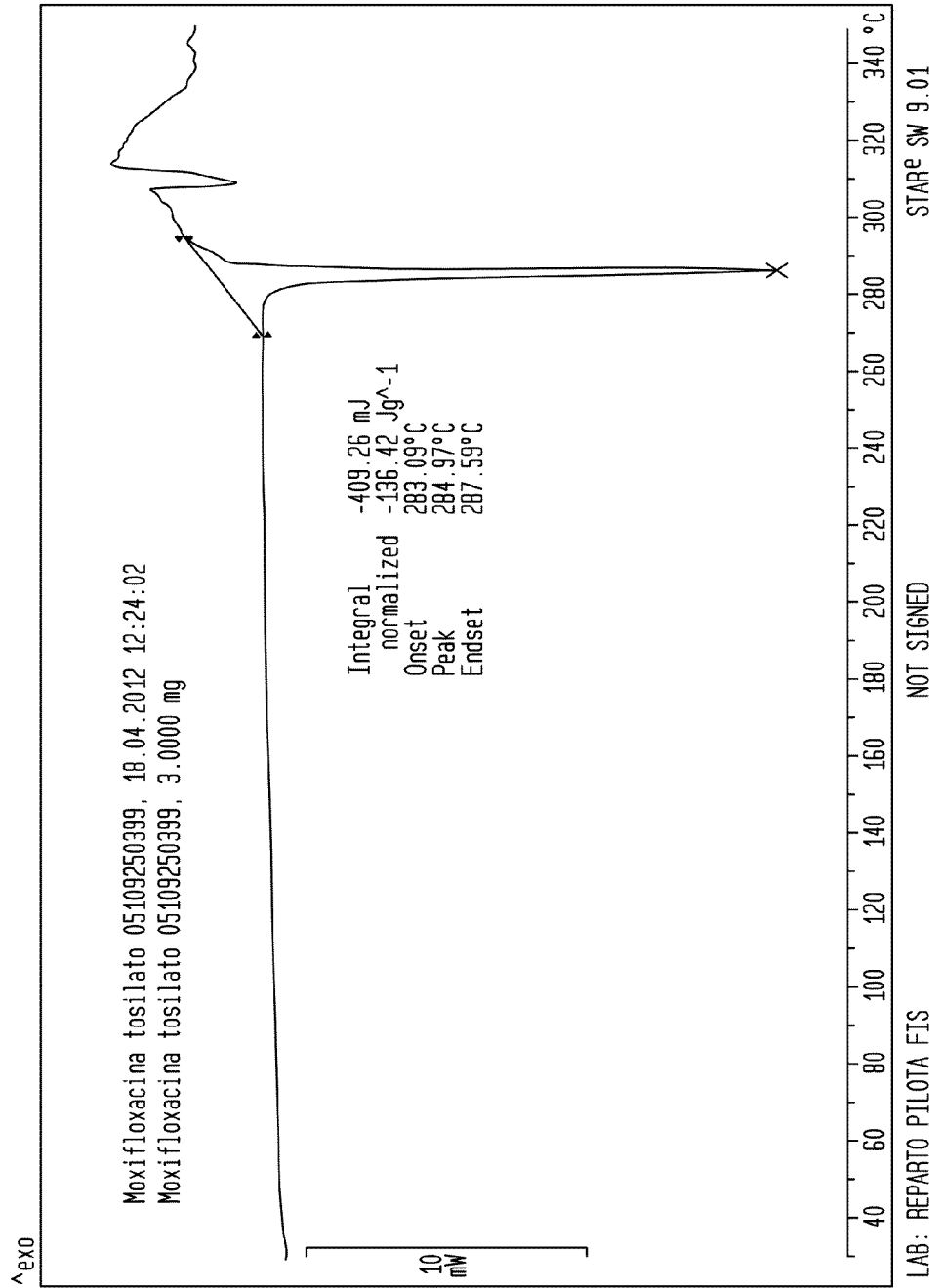
FIG. 6 shows a Differential Scanning calorimetry (DSC) curve of moxifloxacin tosylate.
Figure 7:
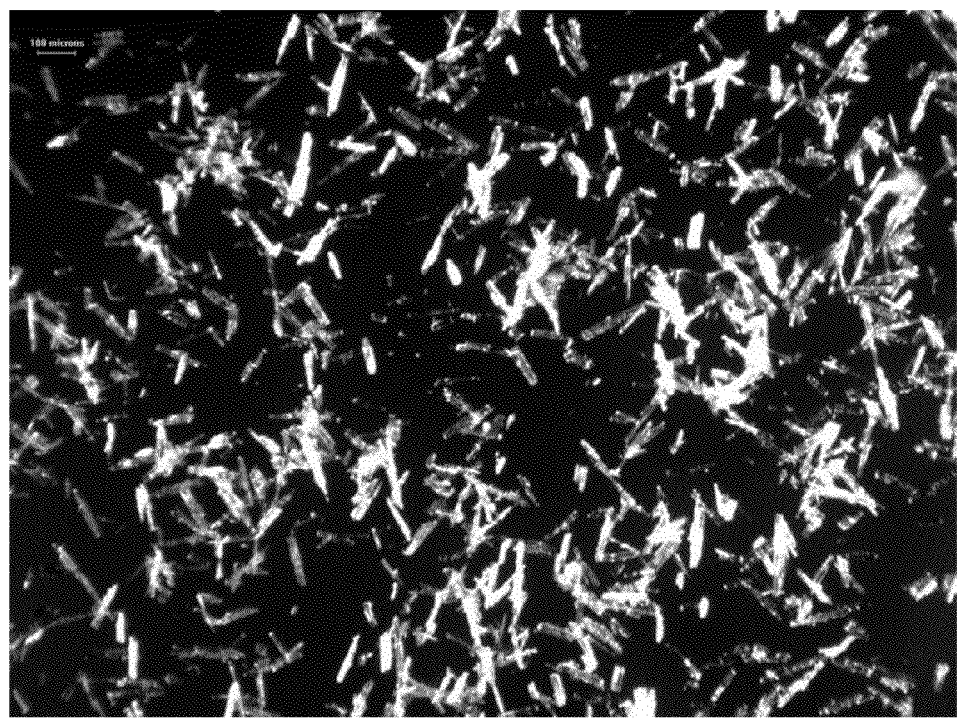
FIG. 7 shows an image acquired with an optical microscope of moxifloxacin tosylate crystal powder.

This crystalline solid has a melting point of 283° C. determined by DSC (onset) (see FIG. 6) and presents a needle-shaped crystal habit (see FIG. 7).

Purified moxifloxacin tosylate typically has K.F.<0.10%, Loss of Drying (LOD)<0.20% (w/w), HPLC purity>99.3% (A %), N-methyl impurity of formula (VII) about 0.30% (HPLC A %) and specific optical rotation comprised in the range of −100° to −106°.

Moxifloxacin hydrochloride prepared according to embodiments of the present invention does not contains ppm of genotoxic impurities such as the C1-C4 alkyl esters of p-toluenesulphonic acid, particularly methyl, ethyl and isopropyl p-Toluenesulphonate. The same is true of the corresponding moxifloxacin base and moxifloxacin tosylate. The GC-MS method employed for this determination is described in Example 7 and allows for the detection of 0.4 ppm of these potential impurities either in moxifloxacin salts such as the hydrochloride, tosylate, etc. or moxifloxacin base.

The absence of C1-C4 alkyl esters of p-toluenesulphonic acid or amounts lower than 10 ppm of these impurities is important for the commercial product since such impurities may be genotoxic and since the product should conform to the ICH, EMA and FDA Guidelines on genotoxic impurities. To our knowledge, these impurities have never been investigated with respect to moxifloxacin and salts thereof.

It has also been surprisingly discovered that moxifloxacin tosylate is a process intermediate that itself may have therapeutic value, in particular for use as an antibacterial agent which may be included in pharmaceutical compositions which also may comprise one or more pharmaceutical carries and/or excipients.

Further reduction in the amount of the N-methyl impurity of formula (VII) to values below 0.15% may be achieved in the step of preparing moxifloxacin hydrochloride. Or, when starting from moxifloxacin containing more than about 1.2% of impurity of formula (VII), it may be achieved in the optional purification step.

Moxifloxacin hydrochloride obtained according to the embodiments of the present invention, thus may comprise the impurity of formula (VII) in a range between about 0.05% and about 0.15%, in other embodiments, between about 0.06% and about 0.14%, and in other embodiments between about 0.06% and about 0.09%, may be conveniently used for the preparation of pharmaceutical formulations also comprising one or more pharmaceutically acceptable excipients and/or carriers.

Moxifloxacin hydrochloride obtained according to the embodiments of the present invention thus may be used in medicine, and in particular as an antibacterial agent, given that the formula (VII) impurity content complies with ICH Q3A guidelines regarding impurities in pharmaceutically active ingredients.

Methods according to embodiments of the present invention described in Example 3, provide moxifloxacin hydrochloride in anhydrous form, having an HPLC purity equivalent to 99.80% for which all impurities are below 0.10%. Accordingly, this compound is pharmaceutically acceptable.

Furthermore, the compound of formula (IV)

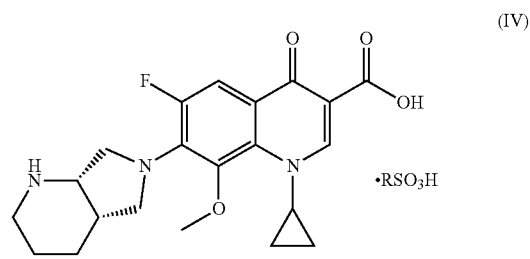

(IV)

in which R is C1-C12 linear, or branched alkyl or is an aryl and in which, for example, R is chosen among C1-C4 alkyl, phenyl and tolyl can be used in medicine, particularly for use as an antibacterial agent. Also moxifloxacin naphtalendisulphonate (2:1) may be used for the same medical uses. Such compounds include moxifloxacin mesylate and moxifloxacin tosylate. These compounds may be formulated in pharmaceutical compositions comprising one or more pharmaceuticals excipients and/or carriers. These formulations may be employed for oral or topical use (e.g. tablets and creams, respectively). For example, an oral formulation may include moxifloxacin tosylate, lactose monohydrate, microcrystalline cellulose, croscarmellose sodium, magnesium stearate, hydroxypropyl methylcellulose, titanium dioxide, polyethylene glycol.

EXAMPLES

Example 1

Synthesis of Moxifloxacin Tosylate of Formula (IV, R=p-MePhenyl or Tolyl)

Synthesis scheme

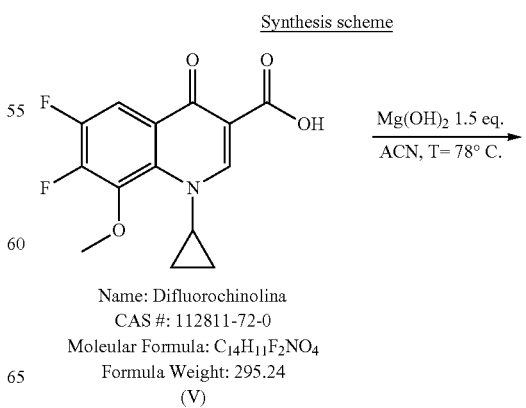

Name: Difluorochinolina
CAS #: 112811-72-0
Molecular Formula: $C_{14}H_{11}F_2NO_4$
Formula Weight: 295.24

(V)

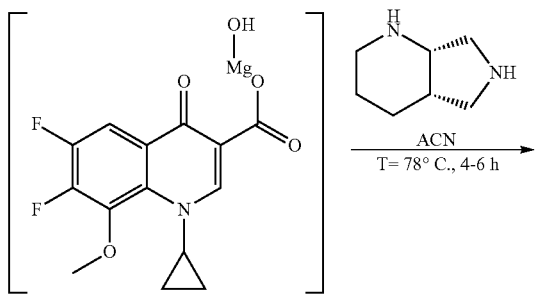

Name: DABCN
CAS #: 151213-40-0
Moleular Formula: $C_7H_{14}N_2$
Formula Weight: 126.20
(VI)

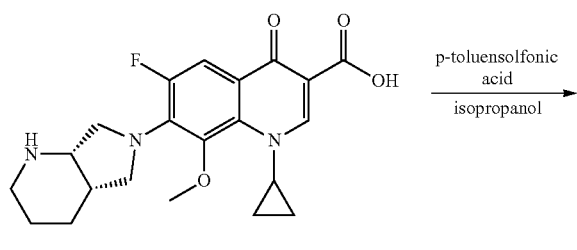

Name: Moxifloxacina Base
CAS #: 151096-09-2
Moleular Formula: $C_{21}H_{24}FN_3O_4$
Formula Weight: 401.43
(II)

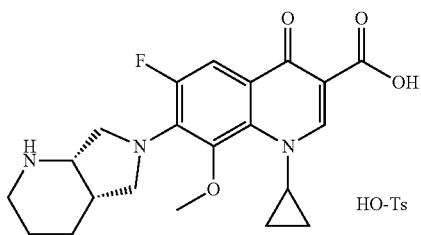

Name: Moxifloxacina HOTs
CAS #: _
Moleular Formula: $C_{21}H_{24}FN_3O_4$
Formula Weight: 573.63
(IV, R = p-MePh)

50.0 g of 1-Cyclopropyl-6,7-difluoro-1,4-dihydro-8-methoxy-4-oxo-3-quinolinic acid of formula (V) (1.0 mol. equiv.), 15.80 g of $Mg(OH)_2$ (1.6 mol. equiv.) and 300 mL of Acetonitrile were introduced into a 4-neck flask provided with a mechanical stirrer, thermometer, cooler and thermostat. Heating was carried out at 78° C. for one hour under slow stirring with the aim of forming the Moxifloxacin complex with Magnesium. A solution formed by 34.20 g of (4aS,7as)-Octahydro-1H-pyrrole[3,4-b]pyridine of formula (VI) and 150 mL of Acetonitrile was dosed in 1 hour. The reaction mixture was left at reflux for another 4 hours. Upon completing the reaction (conversion exceeding 90%) the mixture was cooled at 50° C. and the ACN was distilled under vacuum up to obtaining a soft pasty residue. Such residue was cooled at 0° C. and a cold solution at 0° C. made up of 150 mL of Acetone and 300 mL of Dichloromethane was then added slowly. Stirring was carried out for 10 minutes at room temperature then 2.5 g of dicalite and 2.5 g of acticarbone were added. Stirring was carried out for 10 minutes then filtration was carried out on a dicalite panel. The filtrate was concentrated to dryness in the rotavapor then recovered using 300 mL of dichloromethane. This organic solution was washed using a solution made up of 100 mL of a saturated $NaHCO_3$ solution and 50 mL of purified water. The underlying organic phase containing the product was separated and the aqueous phase was re-extracted using 100 mL of dichloromethane. The organic phases were mixed again and then dried obtaining 71.0 g of Moxifloxacin base, with HPLC purity equivalent to 90.27% and with formula (VII) impurity equivalent to 1.09%.

The solid residue was recovered using 100 mL of purified water and 800 mL of Isopropanol. Heating was carried out at reflux up to complete dissolution. A solution of 26.06 g of paratoluenesulfonic acid (1.1 mol. equiv.) in 100 mL of Isopropanol was dripped at 70° C. in one hour. It was slowly brought to 35° C., then it was left under stirring at 35° C. for one night.

The suspension was paper-filtered at 35° C. and the solid was washed using 100 mL of Isopropanol. The solid was dried in an oven at 50° C. for at least 8 hours.

72.5 g equivalent to a 74.6% molar yield of Moxifloxacin Tosylate were obtained as a hazelnut-coloured solid with HPLC purity equivalent to 98.46% and with a formula (VII) impurity content equivalent to 0.54%.

$^1$H-NMR (400 MHz, DMSO-$d_6$): δ/ppm=0.84-1.24 (m, 4H), 1.70-1.85 (m, 4H), 2.30 (s, 3H), 2.65-2.2.72 (m, 1H), 2.98-3.03 (m, 1H), 3.24-3.28 (m, 1H), 3.52-3.55 (m, 1H), 3.59 (s, 3H), 3.75-3.92 (m, 3H), 4.09-4.20 (m, 2H), 7.12 (d, 1H, j=7.88 Hz), 7.49 (d, 1H, j=8.04 Hz), 7.71 (d, 1H, j=14.13 Hz), 8.69 (s, 1H).

Melting point=273° C. (determined using DSC).

Example 2

Purification of Moxifloxacin Tosylate of Formula (IV, R=p-MePhenyl or Tolyl)

72.5 g of Moxifloxacin Tosylate obtained in Example 1 were dispersed in a solution of 1276 ml of isopropanol and 142 ml of water. The suspension was heated at 80° C. for one hour, then slowly cooled for one night up to 35° C. The suspension remained at 35° C. for 2 hours, then filtering was carried out a paper filter and washing with 142 ml of isopropanol. The solid was dried in an oven at 50° C. for at least 8 hours.

68.2 g equivalent to a 94% molar yield of purified Moxifloxacin Tosylate as a dirty white solid were obtained. The obtained Moxifloxacin Tosylate had an HPLC purity equivalent to 99.30% (A %) with a formula (VII) impurity content equivalent to 0.27%.

Example 3

Synthesis of Moxifloxacin Hydrochloride Starting from Moxifloxacin Tosylate of Formula (IV, R=p-Mephenyl)

Synthesis Scheme

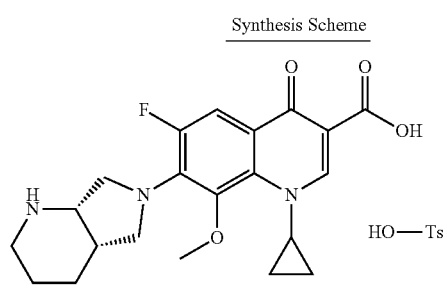

Name: Moxifloxacina HOTs
CAS #: _
Molecular Formula C$_{21}$H$_{24}$FN$_3$O$_4$
Formula Weight: 573.63

(IV, R = p-MePh)

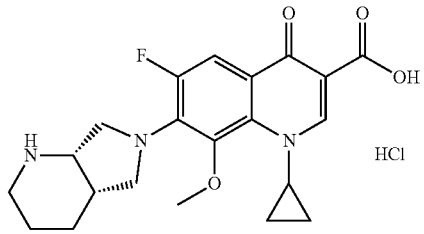

Name: Moxifloxacina HCl
CAS #: 186826-86-8
Molecular Formula C$_{21}$H$_{24}$FN$_3$O$_4$
Formula Weight: 437.89

(I)

68.2 g of purified moxifloxacin tosylate of example 2 (1.0 mol. Equiv.) (HPLC purity equivalent to 99.30% and impurity of formula (VII) equivalent to 0.27%), 409.2 mL of saturated NaHCO3 solution, 136.4 mL of purified water, 409.2 mL of dichloromethane and 68.2 mL of isopropanol were introduced into a 4-neck flask provided with a mechanical stirrer, thermometer, cooler and thermostat. Heating was carried out at 30-35° C. and stirring was carried out for one hour up to complete dissolution. Then the phases were separated and the aqueous phase was extracted using 136.4 mL of Dichloromethane. The organic phases were collected and dried. The obtained solid was recovered with 954.8 mL of Ethanol and 136.4 mL of purified water. Heating was carried out at reflux up to complete dissolution, then it was brought to 60° C. and a solution of 12.3 mL of concentrated hydrochloric acid (32%) (1.05 mol. equiv.) and 136.4 mL of Ethanol was dripped in 2 hours. It was brought to r.t in 4 hours, it was left at room temperature for at least 4 hours, then it was cooled at 0° C. and it was left at 0° C. for another 4 hours. The obtained crystal was filtered washing it with 68.2 mL of Ethanol. The obtained salt was dried at 50° C. under vacuum for 24 hours. 44.3 g of moxifloxacin hydrochloride with a molar yield equivalent to 85.1% with HPLC purity equivalent to 99.79% and a formula (VII) impurity content equivalent to 0.08% was obtained. The obtained product does not contain, even at ppm level, any ester of sulfonic acids as an impurity. This is important because it is well-known that such impurities are genotoxic.

Example 4

Preparation of the Impurity of Formula (VII)

Synthesis Scheme

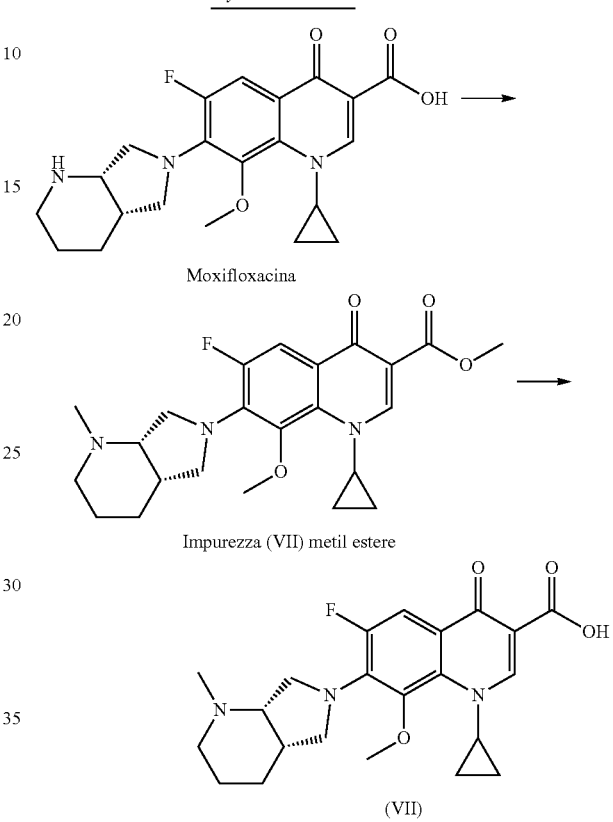

Moxifloxacina = Moxifloxacin
Impurezza (VII) metal estere = (VII) methyl ester impurity 5 g of Moxifloxacin free base (1.0 mol. equiv.), 50 mL of methanol and 3.5 g of potassium carbonate were introduced into a 3-neck flask provided with a mechanical stirrer, thermometer, cooler and thermostat. Cooling was carried out at 0° C. and 6 g of methyl iodide (3.4 mol. equiv.) were dripped. Stirring was carried out for one night at r.t. The reaction was quenched by dripping 50 ml of a 10% sodium hydroxide solution. It was left to stir for one hour and it was brought to pH=8-9 with diluted hydrochloric acid. It was diluted using 200 ml of water and the aqueous phase was washed three times using 100 ml of dichloromethane. Precipitation was carried out by dripping 10 ml of 10% diluted hydrochloric acid, obtaining a light brown precipitate which was paper-filtered and dried in an oven at 50° C. under vacuum. 4.6 g of formula (VII) impurity were obtained.

$^1$H-NMR (400 MHz, DMSO-d$_6$): δ/ppm=0.86-1.11 (m, 4H), 1.44-1.55 (m, 1H), 1.79-1.86 (m, 2H), 1.95-2.05 (m, 1H), 2.82-2.86 (m, 1H), 3.30 (s, 3H), 3.43-3.46 (m, 1H), 3.62 (s, 3H), 3.68-3.74 (m, 2H), 3.94-3.98 (m, 1H), 4.12-4.27 (m, 3H), 7.72 (d, 1H, j=13.06 Hz), 8.68 (s, 1H).

Example 5

HPLC Method for Quantifying the Moxifloxacin Purity and the Formula (VII) Impurity Content in Moxifloxacin Chromatographic conditions:
Column: Zorbax Eclipse Plus C8, 100×4.6 mm, 1.8 μm or equivalent
Column temp: 20° C.
Mobile phase A: TFA 0.1% in $H_2O$
Mobile phase B: TFA 0.1% in MeOH

|  | Time (min) | A (%) | B (%) |
|---|---|---|---|
| Gradient: | 0 | 60 | 40 |
|  | 5.5 | 40 | 60 |
|  | 12 | 0 | 100 |
|  | 13 | 0 | 100 |
|  | 13.5 | 60 | 40 |

Post-run time: 4 minutes
Flow: 1.1 mL/min
Detector: UV at 306 nm
Injection volume: 2.5 μL
Dilutent: $H_3PO_4$ 0.1% in $H_2O$/ACN (7/3)
Duration of analysis: 13.5 min

| Compound | RT (min) | RRT |
|---|---|---|
| Impurity of formula (VII) | 3.56 | 0.92 |
| MOXIFLOXACIN | 3.86 | 1.00 |

Example 6

Synthesis of Moxifloxacin Ethanesulfonate of Formula (IV, R=et)

The procedure is repeated as in Example 1 except that ethanesulfonic acid was used instead of paratoluenesulfonic acid, in the same molar equivalents.

Ethanesulfonate moxifloxacin obtained as a dirty white solid having the following 1H-NMR spectrum.

$^1$H-NMR (400 MHz, DMSO-$d_6$): δ/ppm=0.83-0.90 (m, 1H), 1.02-1.22 (m, 6H), 1.67-1.1.85 (m, 4H), 2.35-2.4 (q, 2H, j=7.42 Hz), 2.63-2.70 (bs, 1H), 2.95-3.00 (m, 1H), 3.22-3.25 (m, 1H), 3.51-3.58 (m, 4H), 3.74-3.92 (m, 3H), 4.03-4.17 (m, 2H), 7.70 (d, 1H, j=14.17 Hz), 8.67 (s, 1H).

Example 7

GC-MS Method for the Determination of the p-Toluensulphonic Acid Alkyl Esters (Methyl, Ethyl and Isopropyl Esters) in Samples of Moxifloxacin Tosylate, Moxifloxacin Hydrochloride and Moxifloxacin Base Chromatographic conditions (GC Agilent 6890N-MS 5975 Quadrupole):
GC Column: DB 5 (or equivalent) L=30 m ID=0.32 mm FT=0.25 μm, with 1 m precolumn
Injector Temperature: 280° C.;
Oven Program: 70° C. for 1.5 min, 10° C./min to 200° C., 20° C./min to a 300° C., 300° C. for 4 min;
Injector: Splitless mode, with 1.0 min of splitless time.
Carrier Gas: He, 1.8 mL/min, constant flow mode (about 8 psi at 40° C.);
Detector: MS a Single Quadrupole, SIM mode;
SIM Parameter: From 6.0 to 11.20 min-155 e 186 m/z
From 11.20 to 11.75 min-155 e 200 m/z
From 11.75 min-155 e 214 m/z
(Modify the acquisition ranges based on RT of the analytes)
Injection Volume: 3 uL with autosampler, slow injection;
Run Time: 23.5 min;
Solvent: Toluene.

The sample of Moxifloxacine Tosylate or hydrochloride should be treated with $NH_3$(aq)/Toluene.

What is claimed is:

1. A compound of formula (IV):

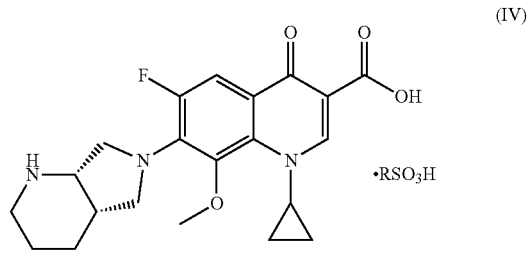

(IV)

wherein R is a C1-C12 linear or branched alkyl or an aryl.

2. The compound of claim 1, wherein R is selected from the group consisting of: C1-C4 alkyl, phenyl and tolyl.

* * * * *

UNITED STATES PATENT AND TRADEMARK OFFICE
CERTIFICATE OF CORRECTION

PATENT NO.        : 8,975,408 B2
APPLICATION NO.   : 14/158939
DATED             : March 10, 2015
INVENTOR(S)       : Gianni Gottardo, Pierluigi Padovan and Sergio Osti It is certified that error appears in the above-identified patent and that said Letters Patent is hereby corrected as shown below:

Title Page, Item (71) Applicant

Applicant's address now reads:
F.I.S. - Fabbrica Italiana Sintetici S.p.A., Alte di Montecchio Maggiore (Vincenz (IT)

Applicant's address should read:
F.I.S. - Fabbrica Italiana Sintetici S.p.A., Alte di Montecchio Maggiore (Vicenza) (IT)

Signed and Sealed this
Twenty-second Day of March, 2016

Michelle K. Lee
*Director of the United States Patent and Trademark Office*